(12) United States Patent
Jackson et al.

(10) Patent No.: US 7,921,717 B2
(45) Date of Patent: Apr. 12, 2011

(54) ULTRASONIC IMAGING SYSTEM

(75) Inventors: John I. Jackson, Menlo Park, CA (US); Lewis J. Thomas, Palo Alto, CA (US); Constantine Simopoulos, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1558 days.

(21) Appl. No.: 11/029,046

(22) Filed: Jan. 3, 2005

(65) Prior Publication Data
US 2006/0173312 A1    Aug. 3, 2006

(51) Int. Cl.
G01N 29/30    (2006.01)
G01N 29/06    (2006.01)
A61B 8/14    (2006.01)

(52) U.S. Cl. .................. 73/602; 600/443; 600/447
(58) Field of Classification Search .......... 73/602; 600/443, 447
See application file for complete search history.

(56) References Cited

U.S. PATENT DOCUMENTS

| | | | |
|---|---|---|---|
| 5,562,096 A | 10/1996 | Hossack et al. |
| 5,703,621 A | 12/1997 | Martin et al. |
| 5,997,478 A | 12/1999 | Jackson et al. |
| 6,030,344 A | 2/2000 | Guracar et al. |
| 6,071,240 A | 6/2000 | Hall et al. |
| 6,086,539 A | 7/2000 | Guracar et al. |
| 6,093,149 A | 7/2000 | Guracar et al. |
| 6,110,118 A | 8/2000 | Guracar et al. |
| 6,155,980 A | 12/2000 | Chiao et al. |
| 6,193,660 B1 | 2/2001 | Jackson et al. |
| 6,193,664 B1 | 2/2001 | Guracar et al. |
| 6,224,556 B1 | 5/2001 | Schwartz et al. |
| 6,241,677 B1 | 6/2001 | Guracar et al. |
| 6,258,029 B1 | 7/2001 | Guracar et al. |
| 6,309,356 B1 | 10/2001 | Ustuner et al. |
| 6,398,733 B1 | 6/2002 | Simopoulos et al. |
| 6,413,218 B1 | 7/2002 | Allison et al. |
| 6,443,894 B1 | 9/2002 | Sumanaweera et al. |
| 6,458,082 B1 | 10/2002 | Jackson et al. |
| 6,464,640 B1 | 10/2002 | Guracar et al. |
| 6,475,148 B1 | 11/2002 | Jackson et al. |
| 6,491,633 B1 | 12/2002 | Krishnan et al. |
| 6,494,841 B1 | 12/2002 | Thomas et al. |
| 6,517,489 B1 | 2/2003 | Phillips et al. |
| 6,527,717 B1 | 3/2003 | Jackson et al. |
| 6,537,218 B1 | 3/2003 | Simopoulos et al. |
| 6,551,246 B1 | 4/2003 | Ustuner et al. |
| 6,579,238 B1 | 6/2003 | Simopoulos et al. |
| 6,589,182 B1 | 7/2003 | Loftman et al. |
| 6,607,488 B1 | 8/2003 | Jackson et al. |
| 6,612,992 B1 | 9/2003 | Hossack et al. |
| 6,645,147 B1 | 11/2003 | Jackson et al. |
| 6,673,017 B1 | 1/2004 | Jackson |
| 6,697,748 B1 | 2/2004 | Rosenberg et al. |
| 6,775,400 B1 | 8/2004 | Zhao et al. |

(Continued)

FOREIGN PATENT DOCUMENTS

JP    2004-154205    6/2004

*Primary Examiner* — Hezron Williams
*Assistant Examiner* — Rose M Miller

(57) ABSTRACT

Disclosed are a system and method of selecting one or more operational parameters of an ultrasonic imaging system. In particular, methods and means are disclosed for automatically or semi-automatically determining a best operating frequency, or for determining whether a system should operate in a fundamental imaging mode or a harmonic imaging mode.

30 Claims, 6 Drawing Sheets

U.S. PATENT DOCUMENTS

| | | |
|---|---|---|
| 2003/0065265 A1 | 4/2003 | Jackson et al. |
| 2003/0158483 A1 | 8/2003 | Jackson et al. |
| 2004/0049110 A1 | 3/2004 | Cai et al. |
| 2005/0228279 A1* | 10/2005 | Ustuner et al. ................ 600/443 |
| 2006/0173313 A1* | 8/2006 | Liu et al. ....................... 600/437 |
| 2007/0173722 A1* | 7/2007 | Ustuner et al. ................ 600/443 |

* cited by examiner

ULTRASONIC IMAGING SYSTEM

BACKGROUND

1. Field

The subject matter disclosed herein relates to ultrasonic imaging systems.

2. Information

"Imaging" refers to a process of capturing visual features of one or more objects of interest. "Ultrasonic imaging" refers to a process of imaging which comprises the processing of acoustic signals. Medical professionals using ultrasonic imaging technology typically employ images of sufficient resolution and clarity for proper diagnosis. An ultrasonic image is formed from transmitting an ultrasonic waveform through tissue and processing resulting reflections and/or transmissions from an object of interest. While using higher frequency transmit waveforms may improve image resolution, the higher frequency waveforms typically introduce increased system noise that may degrade image clarity. System noise also becomes of increasing concern when imaging objects are located at significant depths in tissue (e.g., a distance between a surface of a tissue body and an object of interest within the tissue body). Accordingly, for imaging deep objects, a trade off between resolution quality and image clarity may be made by adjusting the ultrasonic waveform frequency. An ultrasound transducer typically transmits and receives ultrasonic waveforms within a predefined frequency range (e.g., 1.0 to 4.0 MHz) and carrier frequency (e.g., 7.0 to 15 MHz). An operator of an ultrasonic imaging system typically manually adjusts the ultrasonic waveform frequency.

In addition to system noise, the effects of ultrasonic "clutter" may also degrade image quality. Clutter is typically the result of ambient reflections from inert tissue or objects that are not of interest. Typically, bright off-axis targets introduce off-axis scattering that may hinder the ability of commercial ultrasound systems to image desired targets. Echoes from these off-axis targets typically generate broad clutter which may overshadow the signal from the targets, greatly reducing image contrast and/or axial resolution. For example, the rib cage, in cardiac imaging, and the bladder, in abdomen imaging, may result in this off-axis clutter.

An ultrasound imaging system typically operates in a "fundamental" mode in which an ultrasound transducer transmits an ultrasonic waveform at a first carrier frequency and/or bandwidth, and receives and processes reflections at the first carrier frequency and/or bandwidth. An ultrasound imaging system is also typically selectable to operate in a "harmonic" mode in which an ultrasound transducer transmits an ultrasonic waveform at a first carrier frequency and/or bandwidth, and receives and processes reflections at a second, and higher carrier frequency (e.g., the second carrier frequency being an integer multiple of the first carrier frequency such as about twice the first carrier frequency). As clutter may be present predominately at lower frequencies at about the first carrier frequency, by receiving harmonic components of the reflected signal at the higher frequencies (and rejecting lower frequencies of the reflected signal) using a harmonic mode may improve clutter rejection performance. However, the received harmonic signals are typically not as strong as the signals received at the first carrier frequency. Therefore, using a harmonic mode may degrade signal-to-noise performance.

SUMMARY

One embodiment relates to a system and/or method of measuring at least one performance characteristic of a plurality of candidate system configurations of an ultrasound imaging system based, at least in part, upon one or more signals received at an ultrasound transducer while the ultrasound imaging system is configured according to a candidate system configuration. One or more candidate system configurations may be automatically selected for use with the ultrasound imaging system for obtaining an image of an object based, at least in part, upon one or more measured performance characteristics associated with different candidate system configurations. In an alternative embodiment, instead of (or in addition to) automatic selection of candidate system configurations, one or more candidate system configurations may be displayed for selection by an operator based, at least in part, on at least one measured performance characteristics associated with the one or more system configurations. In yet another alternative embodiment, one or more of a plurality of candidate system configurations may be displayed in combination with information relating to one or more measured performance characteristics.

BRIEF DESCRIPTION OF THE FIGURES

Non-limiting and non-exhaustive embodiments will be described with reference to the following figures, wherein like reference numerals refer to like parts throughout the various figures unless otherwise specified.

DETAILED DESCRIPTION

Figure 1:
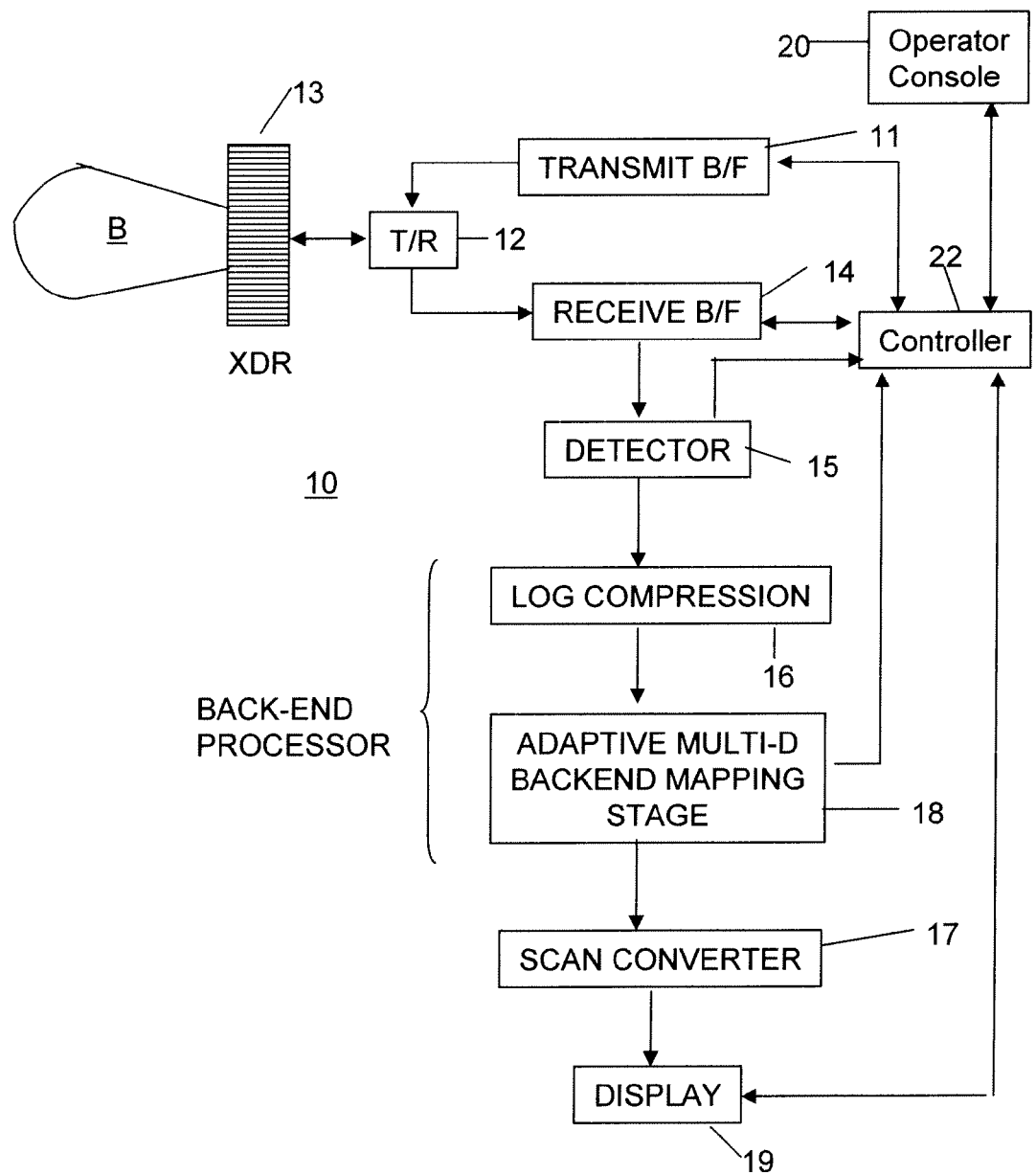
FIG. 1 is a schematic block diagram of a medical diagnostic ultrasonic imaging system according to an embodiment.

Reference throughout this specification to "one embodiment" or "an embodiment" means that a particular feature, structure, or characteristic described in connection with the embodiment is included in at least one embodiment of the claimed subject matter. Thus, the appearances of the phrase "in one embodiment" or "an embodiment" in various places throughout this specification are not necessarily all referring to the same embodiment. Furthermore, the particular features, structures, or characteristics may be combined in one or more embodiments.

An "ultrasound image" as referred to herein relates to a representation of an "object" that is contained within a tissue body that is obtained using an ultrasonic imaging technique. An ultrasound image may be represented as a visual image on a display device or printed media for use in medical diagnostics. An ultrasound image may also be represented as a combination of "pixel values" representing an image intensity in a plurality of "pixel locations" over the image. However, these are merely examples of an ultrasound image and the claimed subject matter is not limited in these respects.

An "ultrasonic waveform" as referred to herein relates to a signal that is capable of traveling in and/or through a tissue body. An ultrasonic waveform in some embodiments may be characterized as having a particular peak power, frequency bandwidth and center or carrier frequency. An ultrasonic waveform may also be transmitted as a pulsed signal (e.g., as a single pulse or series of pulses). However, these are merely examples of an ultrasonic waveform and the claimed subject matter is not limited in these respects.

An "ultrasound transducer" as referred to herein relates to a device that is capable of at least one of transmitting an ultrasonic waveform to an object and/or receiving a reflected waveform from an object. In one embodiment, an ultrasound transducer may comprise a single transducer element or plurality of individual elements dispersed over a surface area formed as a phased array where elements are independently capable of transmitting a portion of an ultrasonic waveform or receiving a portion of a received reflected waveform. In one embodiment, an ultrasound transducer may be configured to "actively scan" an object by transmitting an ultrasonic waveform to the object and receiving the resulting energy reflecting or transmitting from the object. However, these are merely examples of an ultrasound transducer and the claimed subject matter is not limited in these respects.

In one embodiment, an ultrasound transducer may also be configured to transmit an ultrasonic waveform having a particular "transmit frequency" characterized by at least one of a transmit signal bandwidth and/or transmit center frequency of the transmit signal bandwidth. Similarly, an ultrasound transducer may be configured to receive reflected or transmitted energy having a particular "receive frequency" characterized by at least one of a receive signal bandwidth and/or a center frequency of the receive signal bandwidth. However, these are merely examples of a transmit frequency and/or a receive frequency, and the claimed subject matter is not limited in these respects. Also, one or more aspects of a transmit frequency and/or a receive frequency may characterize an "operating frequency" of an ultrasonic imaging system. Accordingly, an operating frequency may characterize either a transmit or receive carrier frequency, a transmit or receive bandwidth, or any combination thereof.

A "desired imaging depth" as referred to herein relates to the depth of an object in a body of tissue to be imaged. For example, a desired imaging depth may relate to the depth of an organ in tissue comprising a distance between a surface of an imaging transducer and a portion of a surface of the organ. Also, a desired imaging depth may be determined from data inputs to an imaging system from an operator or technician to specify a depth within a tissue that is of interest for imaging purposes. However, these are merely examples of a desired imaging depth and the claimed subject matter is not limited in these respects.

A received signal may be processed for the detection of information in the presence of "noise" or "system noise" that is combined with the received signal. Sources of system noise may arise from a variety of origins including, for example, noise from ambient temperature of a tissue body that is being imaged or internal component noise from a device that receives and/or processes the signal. System noise may have particular spectral characteristics, such as a white noise or colored noise. However, these are merely examples of noise, system noise and/or sources of such noise, and the claimed subject matter is not limited in these respects.

To obtain a quality image (e.g., for the purposes of medical diagnostics) a "noise tolerance threshold" may define a quantity of noise such that imaging in the presence of system noise below the noise tolerance results in a received signal-to-noise ratio to enable obtaining the quality ultrasound image. A noise tolerance threshold may be expressed in any one of a variety of forms including, for example, as absolute noise power and/or a gain with respect to the strength of a desired signal (e.g., expressed as decibels) that may be used to express a quantity or level of noise. However, these are merely examples of how a noise tolerance threshold may be expressed and the claimed subject matter is not limited in these respects.

A "system configuration" as referred to herein relates to one or more parameters defining the operation of an embodiment of an ultrasound imaging system. For example, a system configuration may be characterized by one or more operating frequencies that may be used for imaging an object using an ultrasound imaging system. Also, a system configuration may be characterized by the use of either a fundamental or harmonic imaging mode. Also, a system configuration may be characterized as any combination of operating frequency definition and/or imaging mode definition. However, these are merely examples of system configuration embodiments and the claimed subject matter is not limited in these respects.

A "measured noise level" as referred to herein relates to a measurement of one or more components of noise and/or system noise. For example, in an embodiment, a measured noise level may be obtained from signals received at an ultrasonic transducer while an ultrasound imaging system is operating according to a system configuration embodiment. Thus, as previously indicated, a measured noise level may be expressed as an absolute noise power and/or as a gain relative to the power of a signal with information. However, these are merely examples of a measured noise level and the claimed subject matter is not limited in these respects.

A "clutter indicator" as referred to herein relates to a metric that may indicate a degree of the presence of clutter in an ultrasound image. For example, a clutter indicator may be measured while an ultrasound imaging system is configured according to one or more system configuration embodiments. However, this is merely an example of how a clutter indicator measurement may be determined and the claimed subject matter is not limited in these respects.

A "performance characteristic" as referred to herein relates to a metric that is indicative of a system's ability to complete or substantially complete a task or mission or affect one or more qualities of a system's. With an ultrasound imaging system, for example, indications of the degree of system noise or clutter may provide a performance characteristic which is indicative of the ultrasound imaging system to provide a quality image. However, these are merely examples of a performance characteristic and the claimed subject matter is not limited in these respects.

One or more aspects of an embodiment of an ultrasonic imaging system may be set by an operator or technician at an operator console. For example, the operator or technician may set one or more ultrasonic waveform parameters or select an imaging mode (e.g., fundamental versus harmonic) based, at least in part, upon the appearance of an image on a display or other information. Alternatively, an embodiment of an ultrasonic imaging system may "automatically" adjust or select one more of these system parameters or a system configuration embodiment based, at least in part, for example, particular measurements being made from signals received at an ultrasound transducer. Such an automatic adjustment or selection of system inputs or a system configuration may be caused to occur without a specific selection or action of an operator or technician. However, this merely an example of an automatic adjustment and/or selection and the claimed subject matter is not limited in this respect.

Briefly, one embodiment relates to a system and/or method of measuring at least one performance characteristic of a plurality of candidate system configuration embodiments of an ultrasound imaging system embodiment based, at least in part, upon one or more signals received at an ultrasound transducer while the ultrasound imaging system is configured according to the candidate system configuration embodiments. One or more of the candidate system configuration embodiments may then be selected for use with the ultrasound imaging system embodiment for obtaining an image of an object based, at least in part, upon a comparison of the at least one performance characteristic associated with the candidate system configuration embodiments. However, this is merely an example embodiment and the claimed subject matter is not limited in these respects.

In an alternative embodiment, instead of, or in addition to, automatic selection of one or more of the candidate system configuration embodiments, one or more of the candidate system configuration embodiments may be displayed for selection by an operator based, at least in part, on the at least one measured performance characteristics associated with the one or more system configuration embodiments. In yet another alternative embodiment, one or more of the plurality of candidate system configuration embodiments may be displayed in combination with information relating to the one or more measured performance characteristics. However, these are merely additional alternative embodiments and, again, other embodiments are possible and not limited in these respects.

FIG. 1 is a schematic block diagram of a medical diagnostic ultrasonic imaging system according to an embodiment 10. A transmit beamformer 11 transmits ultrasonic waveforms via a transmit/receive switch 12 and a transducer array 13. Transducer array 13 may produce ultrasonic pulses in response to the transmit waveforms which are directed into or toward an object B to be imaged. Returning echoes from object B impinge upon transducer array 13, which converts these echoes into receive signals that are received at a receive beamformer 14 via transmit/switch 12. Receive beamformer 14 may apply appropriate delays and phase shift signals from individual elements of the transducer 13 to result in the receive signals from selected locations within the object B to sum coherently. These beamformed signals are applied to an amplitude detector 15 and a back-end processor that includes a log compression device 16 and an adaptive multi-dimensional back-end mapping stage 18 before being applied to a scan converter 17. Scan converter 17 generates display values upon a grid appropriate for a display 19. It is understood that this is merely an example of an imaging system embodiment, and many other embodiments are possible and included within the scope of the claimed subject matter.

Elements 11-19 may take any suitable form and are not limited to any particular implementation. For example, transmit and receive beamformers 11 and 14 may be constructed as analog and/or digital devices, and any suitable transducer array may be used, including a single-element transducer array and/or phased arrays of various dimensions. Also, system embodiment 10 may include additional elements in the signal path between transducer array 13 and display 19, and selected ones of the illustrated elements may be deleted or the order of some of the elements may be changed. For example, the order of the back-end processor and scan converter 17 may be altered.

By applying appropriate delays and/or coefficient weights to signals applied to the elements of transducer array 13, transmit beamformer 11 may result in the transducer array 13 transmitting an ultrasonic waveform in a "transmit beam" having a particular angular direction (e.g., angular orientation of a main lobe). Similarly, by applying appropriate delays and/or coefficient weights to signals received at the transducer array 13, receive beamformer 14 may emphasize the reception of signal reflections from objects in a particular angular direction to create, in effect, a "receive beam."

An operator console 20 enables an operator to provide input data for defining parameters for obtaining an ultrasonic image. Such parameters may include, for example, the depth of an object to be imaged within body tissue, manually selected operating frequencies and the like. A controller 22 may define modes of operation for the ultrasonic imaging system embodiment based, at least in part, upon parameters from the operator console and information monitored from the back-end processor, detector 15, and/or transmit and receive beamformers 11 and 14. For example, the controller 22 may determine frequencies of an ultrasonic imaging waveform to be employed by the transmit and receive beamformers 11 and 14 (e.g., pulse carrier frequency and bandwidth), modes of operation (e.g., fundamental imaging or harmonic imaging modes), beamforming parameters for the transmit and receive beamformers 11 and 14 (e.g., angular direction of beam and power), the portion of an image to be displayed on the display 19, and/or other modes of operation.

According to an embodiment, controller 22 may provide operational control signals to the transmit and receive beamformers 11 and 14 to define certain operational parameters. For example, controller 22 may determine one or more ultrasonic waveform parameters to employ such as, for example, a center carrier frequency and/or bandwidth (for transmit and/or receive), pulse repetition frequency, pulse waveform duty cycle and transmit power. Also, controller 22 may determine one or more scanning or beamforming parameters such as, for example, transmit and/or receive beam angles.

Controller 22 may comprise a microprocessor or microcontroller that is capable of executing machine-readable instructions from a storage medium for performing the aforementioned processes of defining modes of operations. Alternatively, controller 22 may comprise one or more application specific integrated circuits (ASICs), field programmable gate array (FPGA) devices, application specific programmable devices, and/or any other combination of hardware, software and/or firmware capable of providing logic for performing the aforementioned processes. However, these are merely examples of how a controller may be implemented in an ultrasonic imaging system and the claimed subject matter is not limited in this respect.

Figure 2:
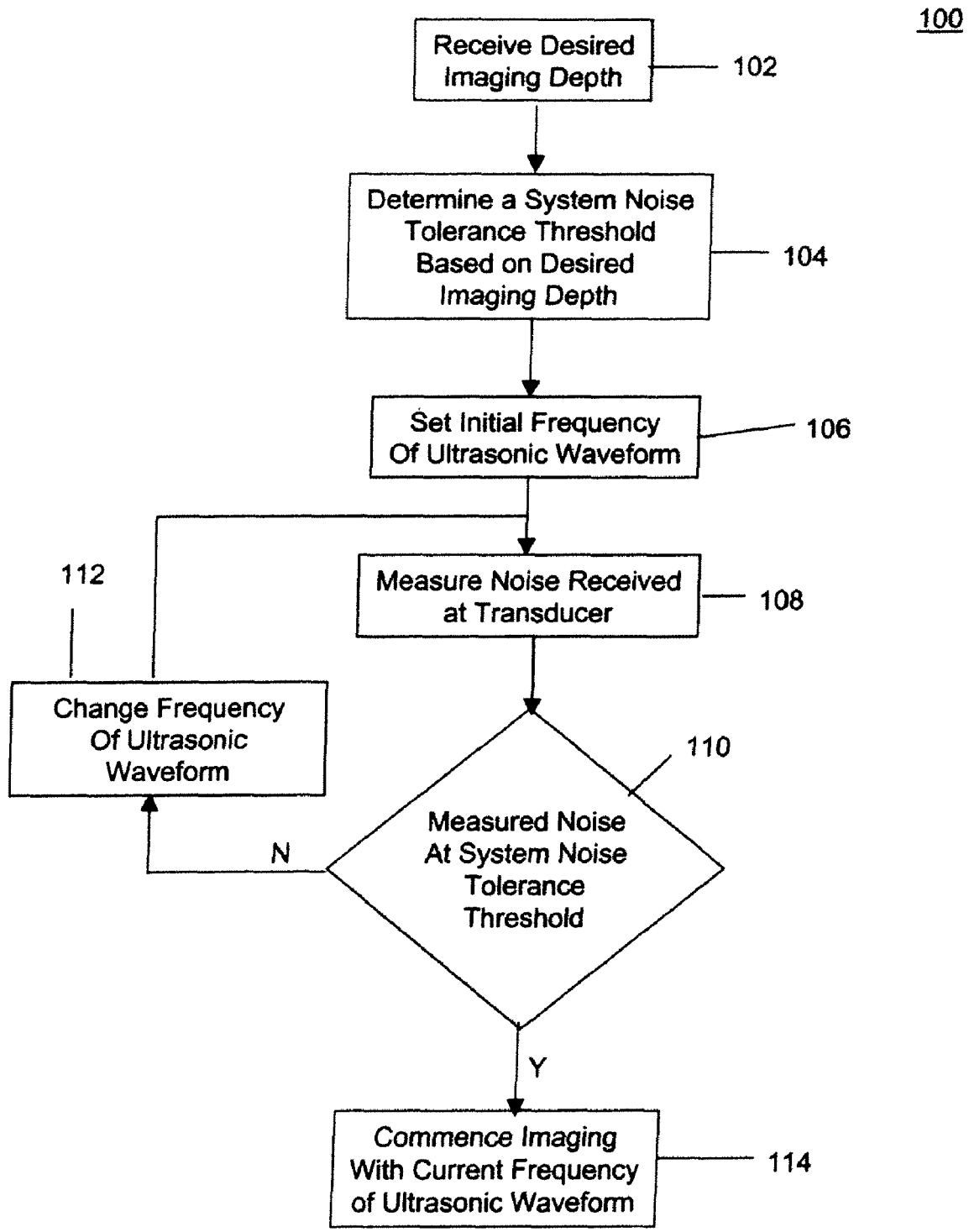
FIG. 2 is a flow diagram illustrating an embodiment of a process to select an operating frequency of an ultrasonic imaging system according to the embodiment shown in FIG. 1.

FIG. 2 is a flow diagram illustrating an embodiment of a process to select an operating frequency for the ultrasonic imaging system embodiment shown in FIG. 1. Such a selected operating frequency may define a transmit frequency and/or a receive frequency, a carrier frequency and/or a bandwidth. Such an operating frequency may also characterize combinations of frequency parameters in a system configuration embodiment such as, for example, a transmit carrier and/or bandwidth, receive carrier and bandwidth, and/or combinations of these parameters for both transmit and/or receive frequencies. In the presently illustrated embodiment, the controller 22 may execute and/or control process embodiment 100 in response to operator input data from operator console 20. However, process embodiment 100 may be initiated by any one of several events such as, for example, a detection of a change in one or more system parameters (e.g., display depth, transducer transmitter power and/or a detection of a change in the image) or on a set period.

At block 102, an operator may indicate a desired imaging depth (e.g., corresponding to the depth of an object of interest within a tissue body) at operator console 20. Based, at least in part, upon the desired imaging depth, block 104 may determine a system noise tolerance threshold. Those of ordinary skill in the art of ultrasonic imaging system design should appreciate that the impact of system noise becomes increasingly problematic as the desired imaging depth increases. For example, for obtaining an image of sufficient quality a given ultrasonic imaging system embodiment may tolerate a higher system noise when obtaining a relatively shallow image while tolerating only a significantly lower system noise when obtaining a relative deep image. Accordingly, based, at least in part, on a desired imaging depth, block 104 may determine a system noise tolerance threshold, although other factors may also affect the determination.

According to an embodiment, block 104 may be implemented from a look-up table that references selectable imaging depths and corresponding noise tolerance thresholds. Such system noise tolerance thresholds may be determined by a manufacturer through experimentation (e.g., adjusting system noise levels while viewing images on a display of objects of different depths) and provided as default parameters based, at least in part, on imaging depths (to be selected by the operator). The noise tolerance thresholds may also be programmable or adjustable by a technician or operator while the particular ultrasonic imaging system is in the field. In another embodiment, the system noise tolerance thresholds may be determined using some other programmed mathematical formula as a function of an imaging depth and/or other parameters.

In another embodiment, a noise tolerance threshold may be determined as a function of signal power received from the object to be imaged and/or other parameters. For example, for a given desired imaging depth, a noise tolerance threshold may be associated with a gain with respect to signal power received from the object (e.g., −30 dB or −50 dB below signal power). Based, at least in part, upon some estimate or a priori knowledge of the signal power received from the object, the noise tolerance threshold may be determined from a gain below the signal power to be received from the object. Likewise, the signal power received from the object may be determined or estimated using any of several techniques such as, for example, measuring a return from one or more test pulses or from a look up table, for example.

Block 106 may set an initial operating frequency to be used in obtaining an image. While transducer 13 (FIG. 1) is placed over the object to be imaged (e.g., in contact with a tissue body including the object), controller 22 may set the receive beamformer 14 to receive ultrasonic signals at an initial operating frequency (e.g., directing the receive beam at the object and/or setting receive filter parameters to receive at the initial operating frequency). Without emissions of a waveform from transmit beamformer 11, block 108 may measure the system noise received at receive beamformer 14. In one embodiment, the system noise may be measured as a local noise mean N(x) as illustrated below with reference to FIG. 3. However, this is merely an example of how system noise may be measured and the claimed subject matter is not limited in this respect.

If the measured system noise is not at about the system noise tolerance threshold as determined at diamond 110 (such as within a specified range, for example) block 112 may change the operating frequency so that the system noise may be measured again at block 108. Otherwise, if the measured noise is at about the system noise tolerance threshold as determined at diamond 110, block 114 may enable imaging the object at the current operating frequency of the ultrasonic waveform (which results in a measured system noise at about the system noise tolerance threshold).

In one embodiment, block 106 may set the initial operating frequency below an expected operating frequency that would result in a measured system noise at the noise tolerance threshold (for the particular desired imaging depth). Block 112 may then incrementally increase the current operating frequency after measurements of the system noise at block 108 until the measured system noise exceeds the system noise tolerance threshold as measured at diamond 110. The current ultrasonic waveform frequency may then be decremented to its previous level (so that the resulting system noise is below the noise tolerance threshold) for use imaging at block 114. In an alternative embodiment, block 106 may set the initial operating frequency above an expected operating frequency that would result in a measured system noise at the noise tolerance threshold as measured at diamond 110. Block 112 may then incrementally decrease the current operating frequency after measurements of the system noise at block 108 until the measured system noise falls below the system noise tolerance threshold. Imaging may then commence at block 114 at the decreased operating frequency.

According to an embodiment, transducer 13 may be capable of operating at a small number of operating frequencies. In an alternative to operations 106 through 110 of the process embodiment 100 illustrated in FIG. 2, transducer 13 may apply available or candidate operating frequencies, and a noise measurement may be made while imaging at these operating frequencies. A relatively high operating frequency resulting in a noise measurement that is below the noise tolerance threshold may then be selected as the operating frequency.

In another alternative embodiment, rather than (or in addition to) automatically selecting an operating frequency to be used in imaging based, at least in part, upon a performance measure (e.g., noise as discussed above), controller 22 may display one or more of the candidate operating frequencies on the operator console 20 along with related performance information. This may allow the operator to select a particular, prescreened operating frequency manually. In yet another alternative embodiment, one or more of the plurality of operating frequencies may be displayed in combination with information relating to the one or more measured performance characteristics.

Figure 3:
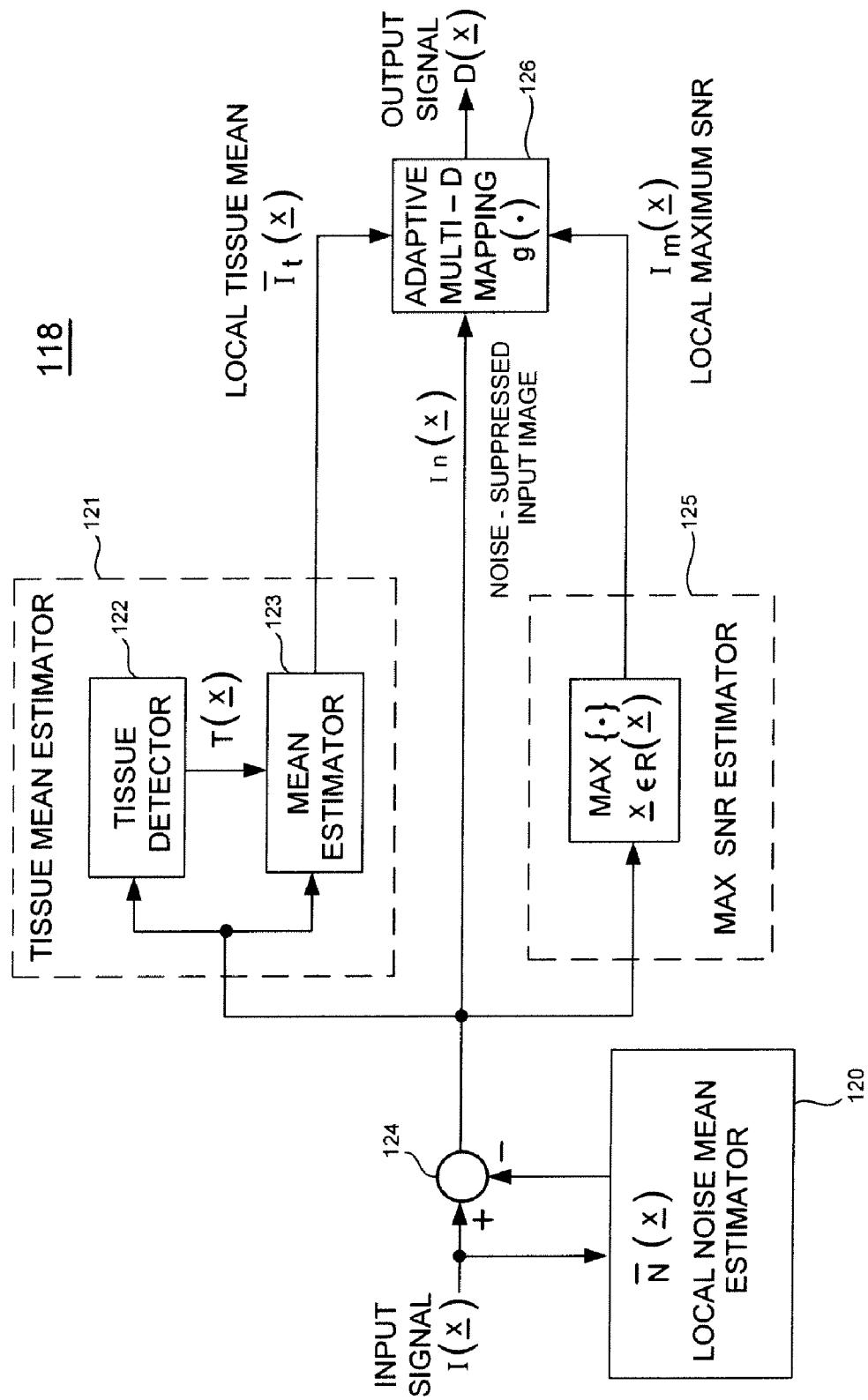
FIG. 3 is a schematic diagram of an embodiment of a backend mapping stage according to the embodiment shown in FIG. 1.

FIG. 3 is a schematic diagram of a backend mapping stage according to an embodiment of the backend mapping stage 18 that may be used for measuring a system noise level according to an embodiment of the ultrasonic imaging system shown in FIG. 1. A backend mapping stage 118 may receive input signals I(x) from a log compression device (e.g., log compression device 16). Simply by way of example, the input signals I(x) may comprise be B-mode image signals. However, the claimed subject matter is not limited to systems that employ B-mode imaging and may apply to other systems employing Doppler imaging and the like.

Input signals I(x) and a local noise mean estimate generated by a local noise mean estimator 120 may be applied to a summer 124. Local noise mean estimator 120 estimates the local noise of the system. In one example, one or more frames of image data may be acquired at transducer 13 without applying transmit signals to the transducer elements of transducer 13. In the absence of an insonifying pressure wave, the resulting input signal forms a noise frame that is a measure of currently-prevailing system noise. This noise frame may then be filtered, such as with a low pass filter, in local noise mean estimator 120 to generate a local noise mean (or measured system noise) N(x). Alternatively, a computer model of the imaging system may be used to estimate a local noise mean N(x) based, at least in part, upon currently prevailing system parameters. This parameter N(x) is subtracted from input signals I(x) at summer 124. The output signal of summer 124 represents noise suppressed input signals $I_n(x)$, which may be applied in parallel to a tissue mean estimator 121, a maximum SNR estimator 125 and an adaptive multi-dimensional mapping stage 126, in this particular embodiment.

Tissue mean estimator 121 processes the noise suppressed input signals $I_n(x)$ to develop an output signal $I_t(x)$ that is indicative of the local mean of $I_n(x)$ for those portions of $I_n(x)$ acquired from soft tissue. Tissue mean estimator 121 includes a tissue detector 122 and a mean estimator 123. Tissue detector 122 may identify those portions of $I_n(x)$ characteristic of soft tissue and generates an output signal T(x) which is in the logic state "1" for values of x associated with soft tissue and is in the logic state 0 for values of x not associated with soft tissue. Tissue detector 122 may take many forms, and it may operate by comparing the variance of $I_n(x)$ with a target value characteristic of soft tissue. Additional information concerning techniques for estimating system noise is described in U.S. Pat. No. 6,579,238 titled "Medical Ultrasonic Imaging System with Adaptive Multi-Dimensional Back-end Mapping." However, the claimed subject matter is not limited in scope to the techniques disclosed.

Figure 4:
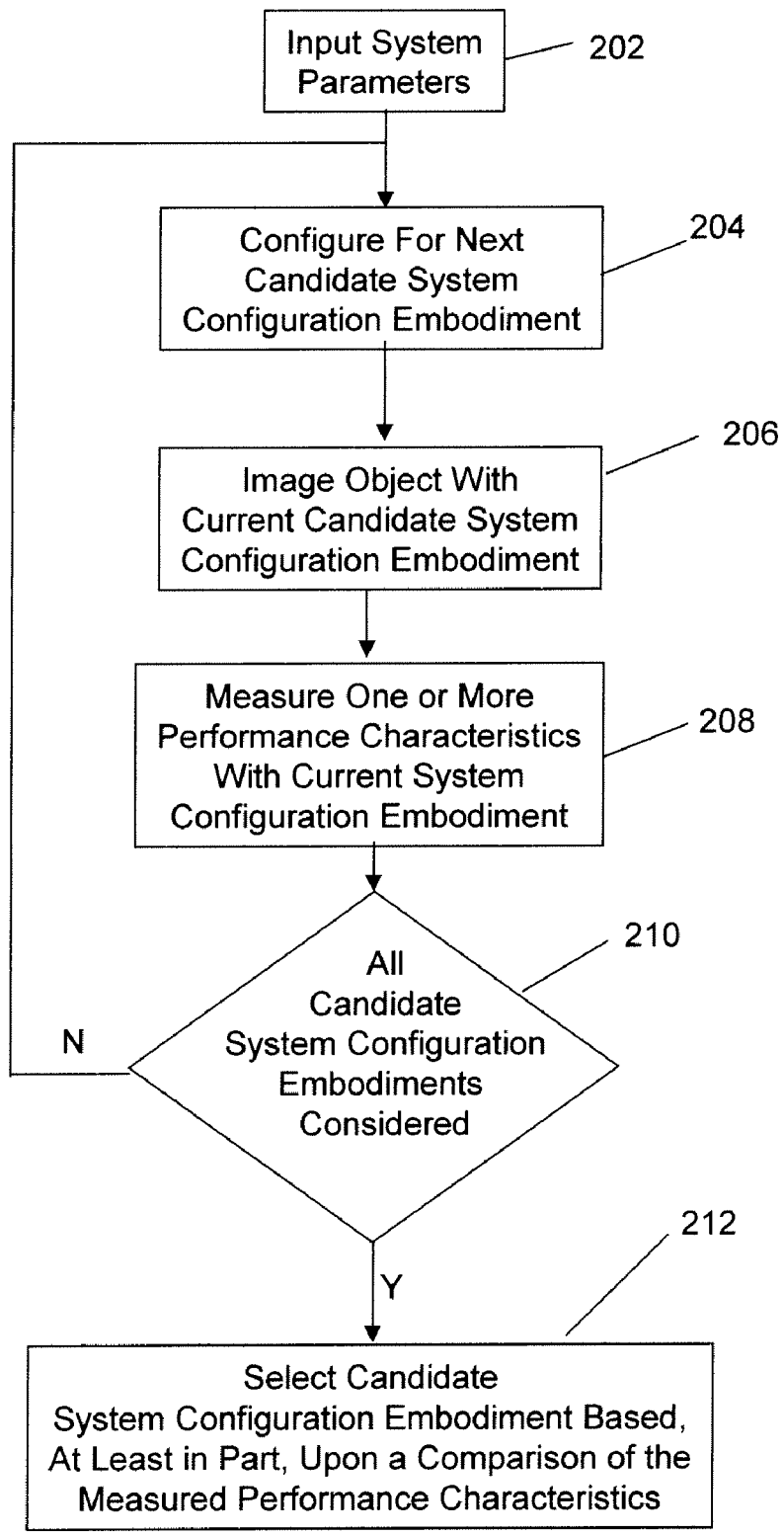
FIG. 4 is a flow diagram illustrating an embodiment of a process to select a system configuration for imaging an object based, at least in part, upon measurements of clutter indicators according to the embodiment shown in FIG. 1.

FIG. 4 is a flow diagram illustrating a process embodiment 200 to select a system configuration embodiment for imaging an object based, at least in part, upon measurements of one or more performance characteristics according to the embodiment shown in FIG. 1. As with the process embodiment 100 of FIG. 2, the process embodiment 200 may be initiated by any one of several events such as, for example, operator input data received at operator console 20, a detection of a change in one or more system parameters (e.g., display depth, transducer transmitter power and/or a detection of a change in the image) and/or on intervals of a set period.

At block 202, controller 22 may configure ultrasound transducer 13 according to some system parameters such as, for example, ultrasonic waveform parameters, transmit power, pulse repetition interval and/or location of an object to be imaged. These parameters may be provided all, or in part, as default parameters, operator data inputs, derived parameters based (at least in part) upon system conditions, or any combination thereof. In one embodiment, for example, an operating frequency may be derived as a function of desired imaging depth and/or other parameters as illustrated above in process embodiment 100 with reference to FIG. 2.

In the presently illustrated embodiment, ultrasonic system 10 may be configured in any one of a plurality of system configuration embodiments. Such a system configuration embodiment may be characterized as employing a fundamental imaging mode or a harmonic imaging mode. Other system configuration embodiments may be characterized as using different operating frequencies. A system configuration embodiment may be characterized as using a fundamental imaging mode with a particular operating frequency as distinguished from another system configuration embodiment using a fundamental imaging mode with a different operating frequency. These system configuration embodiments may also be distinguished from another system configuration embodiment using a harmonic imaging mode with either of the aforementioned operating frequencies or a different operating frequency. A system configuration embodiment may also be characterized as using a particular pulse repetition for the ultrasonic waveform either by itself or in combination with any of the aforementioned system parameters. However, these are merely examples of candidate system configuration embodiments that may be characterized for an ultrasonic imaging system and the claimed subject matter is not limited in these respects.

According to an embodiment, one or more "candidate system configuration" embodiments may be defined for obtaining an image of an object. The one or more candidate system configuration embodiments may be characterized with the attributes of a system configuration as described above. Such candidate system configuration embodiments may be distinct from one another and may result in differing performance characteristics. Accordingly, based on such performance characteristics, a particular one or more of such candidate system configuration embodiments may be selected from among a plurality of candidate system configuration embodiments for obtaining an image of an object. However, this is merely an example of candidate system configuration embodiments, and the claimed subject matter is not limited in this respect.

At block 206, transducer 13 may image the object of interest using the current candidate system configuration embodiment defined at block 204. Based, at least in part, upon the processing of signals received at the receive beamformer 14, block 208 will measure one more performance characteristics resulting from use of the current configuration embodiment to image the object. Such performance characteristics may include, for example, measured system noise (e.g., as system noise measured at block 108) and/or one or more clutter indicators. After a selection of possible candidate system configuration embodiments have been used to image the object (with measurement of the associated performance characteristic(s) being made for candidate system configuration embodiments at block 208) as determined at diamond 210, block 212 may select a candidate system configuration embodiment based, at least in part, upon a comparison of the measured performance characteristics for the candidate system configuration embodiments. For example, system configuration embodiments resulting in lower clutter (as indicated by associated measured clutter indicators) or lowered measured system noise may be favored over system configuration embodiments yielding higher clutter. However, block 212 may select a candidate system configuration embodiment based, at least in part, upon other information in addition to the measured performance characteristics.

In another alternative embodiment, in addition to or instead of automatically selecting a system configuration embodiment based, at least in part, upon a the measured performance characteristics, controller 22 may display one or more of the candidate system configuration embodiments on the operator console 20 along with related performance information (e.g., degree of measured clutter and/or system noise). This may allow the operator to select a particular, prescreened system configuration embodiment manually.

If the system configuration embodiment defined at block 204 includes using a fundamental imaging mode, transmit beamformer 11 may be controlled to transmit an ultrasonic waveform at a transmit carrier frequency and/or transmit bandwidth about the transmit carrier frequency based, at least in part, upon the ultrasonic waveform parameters received at block 202. Receive beamformer 14 may be substantially simultaneously controlled to receive reflections from an object of interest at a receive carrier frequency and/or receive bandwidth that is at about the transmit carrier frequency and/or transmit bandwidth, respectively. The received reflections may then be processed at block 208 to measure (while using the fundamental imaging mode) either a level of clutter or system noise, in the received image signal.

If the system configuration embodiment at block 204 includes using a harmonic imaging mode, transmit beamformer 11 may also be controlled to transmit an ultrasonic waveform at a transmit carrier frequency and/or transmit bandwidth about the transmit carrier frequency based, at least in part, upon the ultrasonic waveform parameters defined in the current system configuration embodiment. Receive beamformer 14 may be substantially simultaneously controlled to receive reflections from an object of interest at a receive carrier frequency and/or receive bandwidth. However, the receive carrier frequency may be higher than the transmit carrier frequency (e.g., 1.5 times the transmit carrier frequency) to emphasize detection of reflections at higher harmonic frequencies. In one embodiment, the receive bandwidth centered about the higher receive carrier frequency may be substantially the same size as that of the transmit bandwidth. In another embodiment, however, the receive bandwidth may be narrower than the transmit bandwidth for greater emphasis on detecting reflections at the higher harmonic frequencies while filtering out reflections at about the fundamental carrier frequency. The received reflections may then be processed at block 208 to measure a level of clutter or system noise present in the received image signal while using the current candidate system configuration embodiment.

To measure the presence of clutter, block 208 may employ any one of several techniques for determining a measurement of an indicator of ultrasonic imaging clutter. For example, a statistical evaluation of histograms image pixel intensity values, coherence factor calculations and/or comparisons of center beam and off beam receive signals while using a center beam transmit signal. These techniques are illustrated in greater detail below. However, it should be understood that these are merely examples of how clutter indicator measurements for an embodiment ultrasonic imaging system may be determined and the claimed subject matter is not limited in these respects.

In one embodiment clutter indicator measurements may be determined based at least in part upon a statistical evaluation of histograms of pixel intensity values. Within a region of interest in an ultrasound image, a pixel value may represent an intensity or degree of darkness for several pixel locations in the region of interest. In one embodiment, for example, pixel locations may be represented by an eight bit value indicating a pixel intensity for the pixel location such that any pixel may have an associated intensity value represented by an integer from 0 to 255. However, this is merely an example of how a pixel intensity may be quantified and the claimed subject matter is not limited in these respects.

With the current candidate system configuration embodiment, the transducer 13 may be controlled to transmit a pulse to the object at center beam (at block 204). Controller 22 may then collect intensity values for pixels over a region of interest (e.g., from the backend mapping stage 18 and/or scan converter 17) for representing the intensities as a first statistical histogram identifying the number of pixels at particular integer intensity values (e.g., 0 to 255).

The resulting histograms of the candidate system configuration embodiments may be statistically compared (at block 212) to determine the relative effectiveness of reducing clutter using the candidate system configuration embodiments. For example, the statistical histogram having a higher variance about a mean pixel intensity may be indicative of greater effectiveness at reducing clutter in the resulting image. In another example, a number of pixels at tail regions in comparison with the number of pixels in a center region may also be indicative of clutter reduction (a histogram having more pixels at the tail ends relative to the center regions may be indicative of more effective clutter reduction). In some embodiments, the statistical comparison may be limited to only contrast among pixels in a central intensity region (e.g., from 100 to 155 with eight bit intensity values). However, these are merely examples of statistical comparisons among histograms of pixel intensity values that may indicate a presence of clutter and the claimed subject matter is not limited in these respects.

Figure 5:
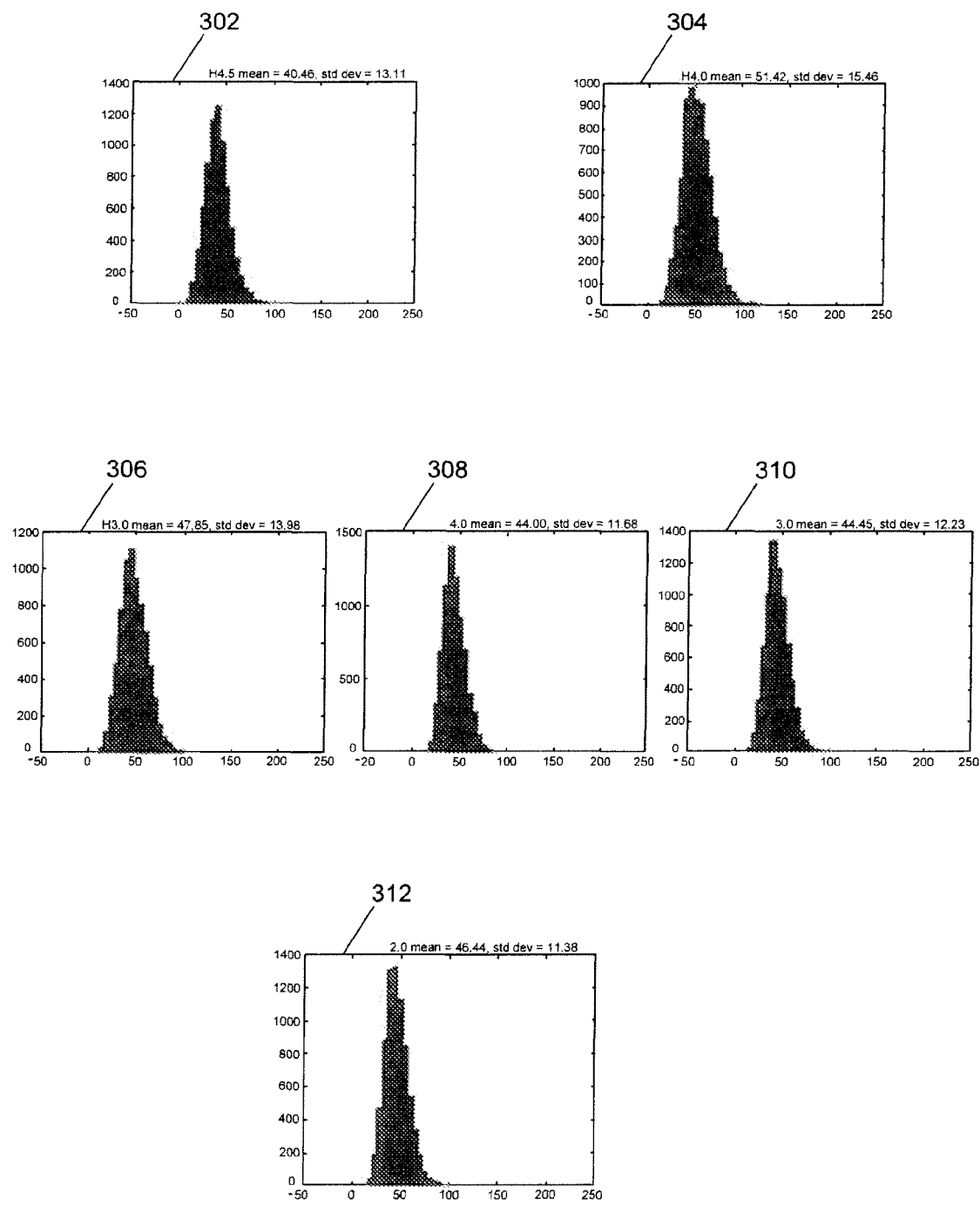
FIG. 5 is a graphical depiction of a statistical analysis of histogram data for measuring clutter indicators for embodiments of candidate system configurations according to the embodiment shown in FIG. 4.

FIG. 5 is a graphical depiction of a statistical analysis of histogram data for measuring clutter indicators for candidate system configuration embodiments according to FIG. 4. The histograms 302 through 312 represent histograms of pixel values received using associated system configuration embodiments in which a pixel value may be an integer from 0 to 255. The mean and variance for each of these histograms is provided as follows:

| Histogram | Mean | Variance |
|---|---|---|
| 302 | 40.48 | 13.11 |
| 304 | 51.42 | 15.46 |
| 306 | 47.85 | 13.98 |
| 308 | 44.00 | 11.88 |
| 310 | 44.55 | 12.23 |
| 312 | 46.44 | 11.38 |

Based at least in part on a comparison of the variance information, the candidate system configuration embodiment producing the histogram 304 may be considered to produce the least amount of clutter since its variance is 15.46 while the candidate system configuration embodiment producing the histogram 312 may be considered to produce the highest amount of clutter since its variance is 11.38.

In an alternative embodiment for measuring clutter indicators at block 208 of process embodiment 200, a coherence factor (CF) may be calculated for an image obtained using the candidate system configuration embodiments at block 206. Generally, a relatively lower CF measurement may indicate a greater presence of clutter while a relatively higher CF may indicate the presence of less clutter. Accordingly, block 212 may select among the candidate system configuration embodiments by (at least in part) favoring candidate system configuration embodiments yielding the relatively higher CF measurments, indicating the presence of less clutter than with candidate system configuration embodiments yielding lower CF measurements.

To obtain a CF measurement at block 208, controller 22 may direct transmit beamformer 11 and 14 to transmit and/or receive a single pulse using the current candidate system configuration embodiment at block 206. Then, a CF may be calculated for the current candidate system configuration embodiment at block 208 as follows:

$$CF = \frac{\left|\sum_i \alpha_i x_i(t)\right|}{\sum_i |\alpha_i x_i(t)|}$$

where:

$x_i(t)$=intensity of the signal received at transducer element i at a sample time t; and $\alpha_i$=apodization constant applied to element i for receive beam forming.

In the presently illustrated embodiment, $x_i(t)$ is expressed as a complex number to represent in-phase and quadrature components of the signal, frequency shifted to baseband and having the appropriate time delay and phase adjustments applied for beamforming, and sampled at element i at time t. In other embodiments, however, a similar CF calculation may be made using radiofrequency signal data from samples that have not been converted to baseband.

Figure 6A:
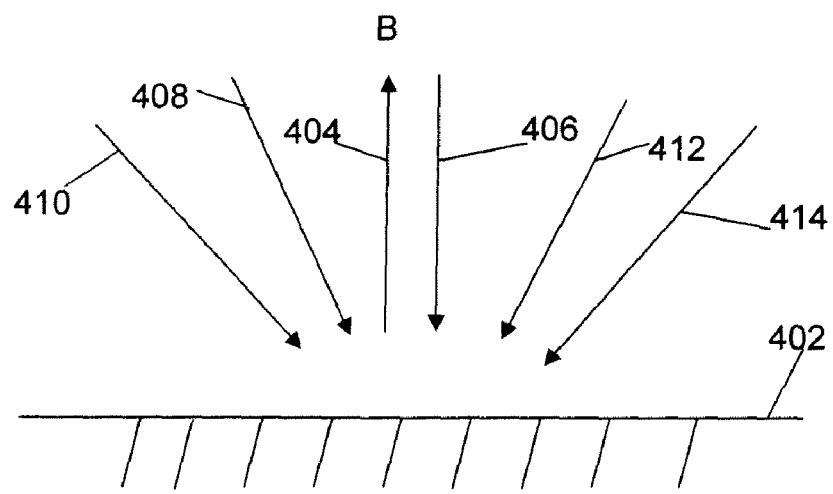
FIGS. 6A through 6C are schematic diagrams illustrating an embodiment of an alternative technique for measuring clutter indicators by comparing the strength of signals received in multiple beam angles.
Figure 6B:
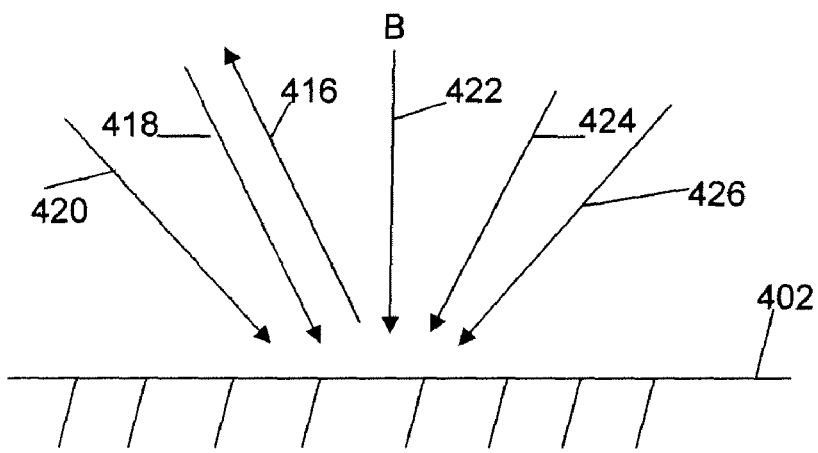
Figure 6C:
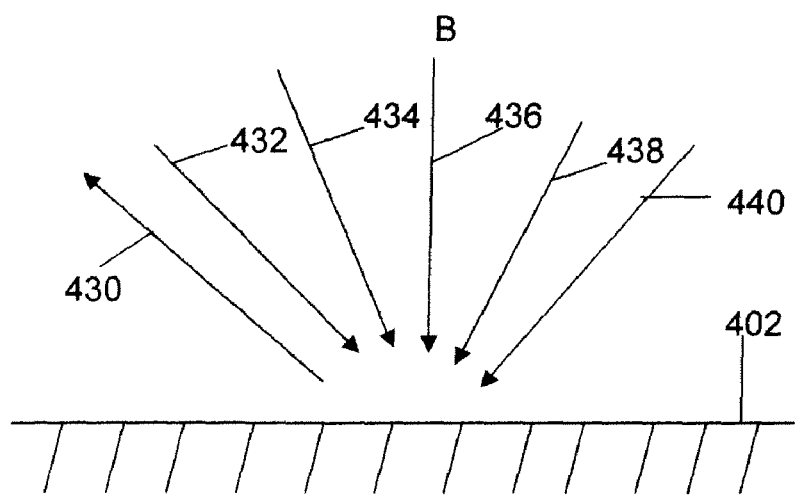

FIGS. 6A through 6C are schematic diagrams illustrating an alternative technique for measuring clutter indicators at block 208 of process embodiment 200 by comparing the strength of signals received in multiple beam angles. At FIG. 6A, a transducer array 402 transmits one or more pulses substantially on a center beam direction 404 to an object B while configured to receive (e.g., forming a beam to receive) a return 406 substantially on center. The transducer array 402 may transmit one or more pulses again directly on the center beam direction 404 while configured to receive on an off center beam directions 408 through 414. Alternatively, a single pulse or set of pulses may be transmitted in the direction 404 while multiple receive beams are substantially simultaneously formed in the receive directions 404 through 414 using parallel beam processing techniques. Received signal strength is measured for the receive directions 406 through 414 (e.g., with backend processor blocks 16 and/or 18).

A similar process may be performed as shown in FIGS. 6B and 6C except that the transmit pulses are directed in off center directions 416 (FIG. 6B) and 430 (FIG. 6C) while obtaining received signal strength measurements in receive directions 418 through 426 in FIG. 6B and in receive directions 432 through 440 in FIG. 6C.

The strength of the signals received in the off beam angles relative to the strength of the signals received at center beam provide an indication of clutter originating from reflections in these respective off beam angles. This may be determined, for example, using a relative clutter level (RCL) to provide a measurement of clutter for a particular candidate system configuration embodiment. Candidate system configuration embodiments yielding a higher RCL in comparison with other configuration may be less favored in the selection at block 212 and candidate system configuration embodiments yielding a lower RCL. Such an RCL may be computed as a ratio of the total off beam energy to the on beam energy as follows:

$$RCL = \frac{\sum_a \sum_d x_a(d)}{\sum_b \sum_d x_b(d)}$$

where:
a=the beams received from directions other than the transmit beam direction;
b=the beams received from the transmit beam direction;
d=the depths at which samples are measured along each receive beam;
$x_a(d)$=the detected and log compressed signal value from beam a and depth d; and
$x_b(d)$=the detected and log compressed signal value from beam b and depth d.

Of course, this is merely an example of possible approach for determining an RCL and the claimed subject matter is not limited in this respect. For the candidate system configuration embodiments, a measure of these clutter indications may be compared among measurements generated from other candidate system configuration embodiments. Accordingly, block 212 may select among the candidate system configuration embodiments at least in part by favoring candidate system configuration embodiments yielding a lower level of clutter expressed by its measurement over candidate system configuration embodiments yielding a higher level of clutter expressed lower CF measurements expressed by its measurements.

While there has been illustrated and/or described what are presently considered to be example embodiments of the claimed subject matter, it will be understood by those skilled in the art that various other modifications may be made, and equivalents may be substituted, without departing from the true scope of the invention. Additionally, many modifications may be made to adapt a particular situation to the teachings of the claimed subject matter without departing from the subject matter that is claimed. Therefore, it is intended that the patent not be limited to the particular embodiments disclosed, but that the it includes all embodiments falling within the scope of the appended claims.

What is claimed is:

1. A method comprising:
measuring at least one performance characteristic of a plurality of candidate system configurations of an ultrasound imaging system based, at least in part, upon one or more signals received at an ultrasound transducer with the ultrasound imaging system serially configured and operating in each of the plurality candidate system configurations; and
automatically selecting one of the candidate system configurations in imaging an object based, at least in part, on the measured at least one performance characteristic.

2. The method of claim 1, wherein said measuring at least one performance characteristic of the plurality of candidate system configurations further comprises:
determining a noise tolerance threshold for obtaining an ultrasound image of the object;
measuring a resulting system noise for the candidate system configurations; and
comparing the measured system noise for the candidate system configurations to the noise tolerance threshold.

3. The method of claim 2, wherein the method further comprises determining the noise tolerance threshold based, at least in part, on a desired imaging depth for the ultrasound image of an object.

4. The method of claim 2, wherein the method further comprises determining the noise tolerance threshold based, at least in part, on an estimate of a strength of signal received from an object.

5. The method of claim 1, wherein said measuring at least one performance characteristic comprises measuring at least one clutter indicator associated with the candidate system configurations.

6. The method of claim 5, wherein measuring at least one clutter indicator associated with the candidate system configurations further comprises processing the one or more signals received at the ultrasound transducer to obtain first period pixel values for pixels in a region, and wherein the method further comprises automatically selecting the selected system configuration from among the plurality of candidate system configurations based, at least in part, upon a statistical comparison of the obtained pixel values.

7. The method of claim 5, wherein measuring at least one clutter indicator associated with the candidate system configurations further comprises processing the one or more signals received at the ultrasound transducer to determine a coherence factor measurement, and wherein the method further comprises selecting the selected system configuration from among the candidate system configurations based, at least in part, upon a comparison of coherence factor measurements associated with the candidate system configurations.

8. The method of claim 5, wherein measuring at least one clutter indicator associated with the candidate system configurations further comprises:
  transmitting a waveform in a first direction;
  receiving a reflection of the transmitted waveform in the first direction and a second direction different from the first direction; and
  comparing a strength of the reflection received in the first and second directions.

9. The method of claim 1, wherein the candidate system configurations are characterized as having an operating frequency.

10. The method of claim 9, wherein the operating frequency comprises at least one of a transmit carrier frequency and/or a transmit bandwidth.

11. The method of claim 9, wherein the operating frequency comprises at least one of a receive carrier frequency and/or a receive bandwidth.

12. The method of claim 1, wherein the candidate system configurations are characterized as having exactly one of a fundamental imaging mode or a harmonic imaging mode.

13. A method comprising:
  measuring at least one performance characteristic of a plurality of candidate system configurations of an ultrasound imaging system based, at least in part, upon one or more signals received at an ultrasound transducer; and
  displaying one or more of the candidate system configurations based, at least in part, on the measured at least one performance characteristic.

14. The method of claim 13, the method further comprising enabling selection of one of the displayed candidate system configurations in response to operator input data.

15. The method of claim 1, the method further comprising performing said measuring at least one performance characteristic of the plurality of candidate system configurations and said automatically selecting one of the candidate system configurations in response to at least one of a change in an image, an imaging control change, a change in display depth or change in transducer transmitter power, or on intervals of a set period.

16. An apparatus comprising:
  means for measuring at least one performance characteristic of a plurality of candidate system configurations of an ultrasound imaging system based, at least in part, upon one or more signals received at an ultrasound transducer with the ultrasound imaging system serially configured and operating in each of the plurality candidate system configurations; and
  means for automatically selecting one of the candidate system configurations in imaging an object based, at least in part, on the measured at least one performance characteristic.

17. The apparatus of claim 16, wherein the means for measuring at least one performance characteristic of the plurality of candidate system configurations further comprises:
  means for determining a noise tolerance threshold for obtaining an ultrasound image of the object;
  means for measuring a resulting system noise for the candidate system configurations; and
  means for comparing the measured system noise for the candidate system configurations to the noise tolerance threshold.

18. The apparatus of claim 17, wherein the apparatus further comprises means for determining the noise tolerance threshold based, at least in part, on a desired imaging depth for the ultrasound image of an object.

19. The apparatus of claim 17, wherein the apparatus further comprises means for determining the noise tolerance threshold based, at least in part, on an estimate of a strength of signal from an object.

20. The apparatus of claim 16, wherein the means for measuring at least one performance characteristic comprises means for measuring at least one clutter indicator associated with the candidate system configurations.

21. The apparatus of claim 20, wherein the means for measuring at least one clutter indicator associated with the candidate system configurations further comprises means for processing the one or more signals received at the ultrasound transducer to obtain first period pixel values for pixels in a region, and wherein the apparatus further comprises automatically selecting the selected system configuration from among the plurality of candidate system configurations based, at least in part, upon a statistical comparison of the obtained pixel values.

22. The apparatus of claim 20, wherein the means for measuring at least one clutter indicator associated with the candidate system configurations further comprises means for processing the one or more signals received at the ultrasound transducer to determine a coherence factor measurement, and wherein the apparatus further comprises means for selecting the selected system configuration from among the candidate system configurations based, at least in part, upon a comparison of coherence factor measurements associated with the candidate system configurations.

23. The apparatus of claim 20, wherein the means for measuring at least one clutter indicator associated with the candidate system configurations further comprises:
  means for transmitting a waveform in a first direction;
  means for receiving a reflection of the transmitted waveform in the first direction and a second direction different from the first direction; and
  means for comparing a strength of the reflection received in the first and second directions.

24. The apparatus of claim 16, wherein the candidate system configurations are characterized as having an operating frequency.

25. The apparatus of claim 24, wherein the operating frequency comprises at least one of a transmit carrier frequency and/or a transmit bandwidth.

26. The apparatus of claim 24, wherein the operating frequency comprises at least one of a receive carrier frequency and/or a receive bandwidth.

27. The apparatus of claim 16, wherein the candidate system configurations are characterized as having exactly one of a fundamental imaging mode or a harmonic imaging mode.

28. The apparatus of claim 16, the apparatus further comprising means for initiating measurement of the at least one performance characteristic and initiating automatic selection of the one of the candidate system configurations based, at least in part, on the measured at least one performance characteristic in response to at least one of a change in an image, an imaging control change, a change in display depth or change in transducer transmitter power, or on intervals of a set period.

29. An apparatus comprising:
  means for measuring at least one performance characteristic of a plurality of candidate system configurations of an ultrasound imaging system based, at least in part, upon one or more signals received at an ultrasound transducer; and means for displaying one or more of the candidate system configurations based, at least in part, on the measured at least one performance characteristic.

30. The apparatus of claim 29, the apparatus further comprising means for enabling selection of one of the displayed candidate system configurations in response to operator input data.

* * * * *